United States Patent [19]
Schoeters et al.

[11] Patent Number: 5,644,649
[45] Date of Patent: Jul. 1, 1997

[54] PROCESSING METHOD IN RADIOGRAPHIC IMAGE RECORDING SYSTEMS

[75] Inventors: Emile Paul Schoeters, Lier; Lucien Alfred Hayen, Antwerp, both of Belgium

[73] Assignee: AGFA-Gevaert N. V., Mortsel, Belgium

[21] Appl. No.: 907,125

[22] Filed: Jul. 1, 1992

[30] Foreign Application Priority Data

Jul. 15, 1991 [EP] European Pat. Off. .............. 91201865

[51] Int. Cl.[6] .................................................. G06K 9/00
[52] U.S. Cl. ................................................ 382/132; 382/283
[58] Field of Search .................................. 382/6, 30, 128, 382/132, 212, 282, 283; 364/413.13; 378/4, 62; 250/327.2, 484.1

[56] References Cited

U.S. PATENT DOCUMENTS

| | | | |
|---|---|---|---|
| 4,922,915 | 5/1990 | Arnold et al. | 382/6 |
| 5,123,056 | 6/1992 | Wilson | 382/1 |
| 5,150,421 | 9/1992 | Morishita | 382/6 |
| 5,151,947 | 9/1992 | Nagatsuka et al. | 382/6 |
| 5,157,733 | 10/1992 | Takeo | 382/6 |
| 5,163,095 | 11/1992 | Kosaka | 382/6 |
| 5,224,177 | 6/1993 | Doi | 382/6 |

*Primary Examiner*—Yon J. Couso
*Attorney, Agent, or Firm*—William J. Daniel

[57] ABSTRACT

In the digital processing of radiographic images, interpretation of the image is aided by converting the pixels of an original radiographic image into electrical signals generally corresponding to the densities of the individual pixels and adjusting the electrical signals for the pixels constituting a diagnostically non-relevant image zone, selectively of the pixels constituting a diagnostically relevant image zone, as determined by observation of a visualization of the original radiographic images, e.g. by a radiologist viewing such image on the screen of a viewing monitor, to a density level such that when the electrical signals including the adjusted signals are visualized into an image for interpretation, the pixels of the diagnostically non-relevant zone are effectively masked out and light from the non-relevant zone is prevented from interfering with viewing of the relevant zone. Various predetermined configurations, e.g. a rectangle, circle or polygon, can be selected for the relevant zone for generation by identifying a few selected points on the original image being viewed, e.g., opposite corner points for a rectangular, a center point and perimeter point for a circle, etc. The visualized image with the blanked out non-relevant regions can be recorded electronically as a soft copy or photographically as a hard copy on a photographic recording medium. Border regions around the image can be made of maximum density, e.g. black, while the density of the non-relevant zone is adjusted to a lesser but still masking density.

14 Claims, 4 Drawing Sheets

PROCESSING METHOD IN RADIOGRAPHIC IMAGE RECORDING SYSTEMS

DESCRIPTION

1. Field of the Invention

The present invention relates to the field of digital image processing, more in particular to a method enhancing the image quality of radiographic images for medical diagnostic purposes, obtained by means of a digital radiographic system.

2. Background of the Invention

In radiography the interior of objects is reproduced by means of penetrating radiation, which is high energy radiation belonging to the class of X-rays, gamma-rays and high-energy elementary particle radiation, e.g. beta-rays, electron beam or neutron radiation. For the conversion of pentrating radiation into visible light and/or ultraviolet radiographic luminescent substances, called phosphors, are used.

In a conventional radiographic system an X-ray radiograph is obtained by X-rays transmitted imagewise through an object and converted into light of corresponding intensity in a so-called intensifying screen (X-ray conversion screen) wherein phosphor particles absorb the transmitted X-rays and convert them into visible light and/or ultraviolet radiation to which a photographic film is more sensitive than to the direct impact of X-rays.

In practice the light emitted imagewise by said screen irradiates a contacting photographic silver halide emulsion layer film which after exposure is developed to form therein a silver image in conformity with the X-ray image.

More recently an X-ray recording system (commonly called 'digital radiography') has been developed wherein photostimulable storage phosphors are used having in addition to their immediate light emission (prompt emission) on X-ray irradiation the property to store temporarily a large part of the energy of the X-ray image which energy is set free by photostimulation in the form of light different in wavelength characteristic from the light used in the photostimulation. In said X-ray recording system the light emitted on photostimulation is detected photoelectronically and transformed into sequential electrical signals.

The basic constituents of such X-ray imaging system operating with a photostimulable storage phosphor are an imaging sensor containing said phosphor in particulate form normally in a plate or panel, which temporarily stores the X-ray energy pattern, a scanning laser beam for photostimulation, a photoelectronic light detector providing analogue signals that are converted subsequently into digital time-series signals, normally a digital image processor which manipulates the image digitally, a signal recorder, e.g. magnetic disk or tape, and an image recorder for modulated light exposure of a photographic film or an electronic signal display unit, e.g. cathode-ray tube. More details about said system are described in the periodical Radiology, September 1983, p. 833–838, and May 1989, p. 300–302.

In the conventional screen-film radiographic system as well as in the more recently developed digital radiographic system the medical diagnosis executed by the radiologist is based upon the visual inspection of a radiographic image recorded by a radiographic film. The accuracy of said medical diagnosis is generally recognised as depending primarily on the skill and experience of the radiologist and of the technical characteristics of the conventional or digital radiographic system. However, also the practical circumstances wherein the radiographs are actually viewed by the radiologist play an impartant role in the accurate assessment of the diagnostic information recorded in the films, although much less attention is generally paid to these factors. As is set forth in the article 'Film Viewing 1966' by J. Blair Hartley, published in RÖ.–B1., 20 Jahrgang, 2/67, pp 96–99, the application of some simple principal rules in evaluating radiographic films already decreases the frequency of misinterpretations. In said article it was stated that it is ridiculous to expect the human eye to attune itself simultaneously to light emerging through a radiograph and light emitted directly from an optical display unit such as a viewing box, on which said radiograph was put, knowing that the brilliance could vary as much as 1:160. Therefore one of the elementary principles of viewing radiographs was the cutting of masks of varying sizes so that one viewed only the radiograph and not the viewing box plus the radiograph. As the latter was a rather cumbersome method of masking, illuminators with metal blinds built inside have become available which offer more practical means of masking the surrounding light causing undesired dazzle.

In the article 'A self-masking film illuminator' by Keith C. Hammond, M. B., B. S., published in the British Journal of Radiology, May 1974, 47, 283–285 an illuminator is described which automatically masks the light emerging from the illuminator in the surroundings of a radiograph. So the disadvantages caused by the bright light escaping round the radiograph and impairing the radiologist's visual perception are automatically avoided.

Because of the high cost and cumbersome operation, such illuminators have not been put in practical use on a commercial scale. In the article 'Aspects of the interpretation of contrast and detail in Radiographs' by Ove Mattson, published in Acta Radiol. (Diagn.) 38: 447, December 1952, a method for enhancing the diagnostic evaluation of radiographs is proposed, starting from a generally known phenomenon, namely that 'the ability of the eye to discern details in a dark street at night is greatly enhanced if the eye be shaded from the direct light of a nearby street lamp'.

Satisfactory lighting is also essential for the study and evaluation of radiographs, and the ability of discerning detail in a particular illuminated object depends to a large extent on the illumination of the surroundings of said object.

Now apart from various other factors such as undesired reflections by light coming from the radiologist-viewer's side, and unnecessary brightness in the viewing room, the transparent film margins adjacent to the radiographic image produce dazzle which reduces the efficiency of the eye in evaluating the radiograph.

Knowing that the ability of discerning detail was related to the surroundings, it was stated in said article that an increased amount of detail would be discernible in denser areas after shading off the neighbouring and more translucent regions. The best way of obtaining increased evaluation of detail in the denser areas is the masking off of unimportant surrounding regions.

In order to effectively mask off the insignificant part of the field of vision, or to limit the field of vision such that large lighted areas which may create dazzle are excluded, the author of the cited article has designed a cheap and simple viewer permitting i.a. the study of heavily exposed radiographs under optimal viewing conditions. Such viewer consisted of a hood made of cardboard in the shape of a truncated pyramid, one end of which was shaped in such a way as to form a light-proof seal around the eyes, the opposite end of which had a square opening and rested against the image. When such viewer was held close to the radiograph, reflection and dazzle was effectively eliminated, and enhanced diagnostic detail could be discerned on the radiographic image.

Although the advantages of such viewer were recognised, it has not been put into universal use because of the practical inconveniences resulting from its use.

As a conclusion it may be set forth that although the principles according to which a radiograph should be evaluated on an optical display unit such as a viewing box have been known for decades, no practically acceptable solution has yet been put forward. The latter problem is in particular important in the more recently developed digital radiographic system as enhanced radiographic image quality is one of the primary advantages of said system over the conventional radiographic system.

Further this problem is of particular significance in digital radiography in view of the often applied collimation technology. In order to minimize the absorption of X-rays by the patient, only that particular part of the human body a medical X-ray diagnosis whereof is necessary, should be subjected to irradiation; the collimation technique then consists in masking the remaining parts of the patient from the penetration of X-rays.

A technique often applied is limiting the emission of X-rays by using a diaphragm consisting of lamellae near to the X-ray emitting source. Another technique consists in covering the parts of the human body, a medical diagnosis whereof is not required, with the aid of flaps comprising lead foils.

When however one of such collimation techniques has been used and the radiographic image is recorded as a hard copy on film for visualisation on an optical display unit such as a viewing box, the zones in the radiographic image corresponding to the collimated parts of the human body appear as full white zones, causing the dazzling effect described hereinabove.

OBJECT OF THE INVENTION

It therefore is an object of the present invention to provide a method of processing the digital image in a digital radiographic system in such a way that the dazzling effect described above does not occur, whereby the accuracy of the diagnostic evaluation of a radiographic image may be significantly enhanced.

In particular it is an object of the present invention to provide a method resulting in increased evaluation of detail in the radiographic image when visualised either as soft copy on the screen of a review monitor or when visualised as hard copy, when recorded in a photographic recording material by a film recorder, on an optical display unit such as a viewing box.

Further objects and advantages will become apparant from the description given hereinbelow.

SUMMARY OF THE INVENTION

We now have found that the above objects can be achieved by providing a method of processing a radiographic image in a radiographic image recording system wherein electrical signals are converted to density values for visualisation of the radiographic image either as a soft copy on a screen of a console or as a hard copy recorded in a photographic recording material on an optical display unit, said method comprising the step of converting electrical signals of the image points comprised within a diagnostically not relevant image zone within the radiographic image to a density value such that when visualised as either a soft or a hard copy the light transmitted by said image parts from the console screen or the optical display unit is effectively masked off.

According to a preferred embodiment of said method of processing the diagnostically not relevant image zone within the radiographic image is defined as encompassing all image points within the radiographic image that are not comprised within a diagnostically relevant image zone, defined under visual control on a preview monitor.

According to a further preferred embodiment of said method the radiographic image recording system is a system in which a stimulable phosphor is scanned with a stimulating ray and the radiographic image information recorded in the stimulable phosphor is read out and converted into an electric signal upon stimulation thereof. The invention will be illustrated hereinafter for this preferred embodiment.

Further preferred embodiments of the present invention are set forth in the detailed description given hereinafter.

DETAILED DESCRIPTION OF THE INVENTION

Particular aspects of the present invention and preferred embodiments hereof will be explained hereinbelow with reference to the drawings in which FIG. 1 generally illustrates an apparatus in which the method of the present invention is applied.

Figure 1:
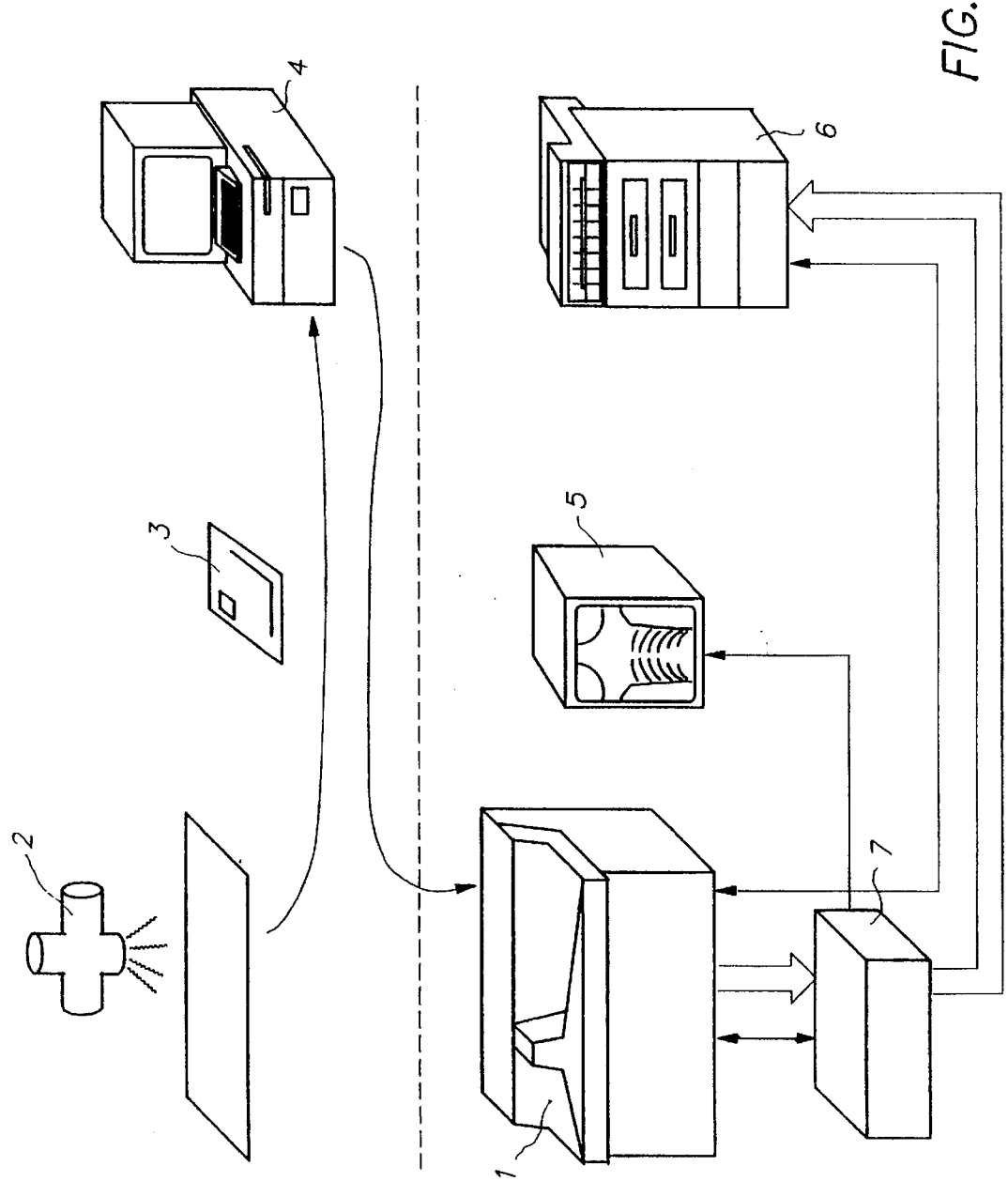
Figure 2:
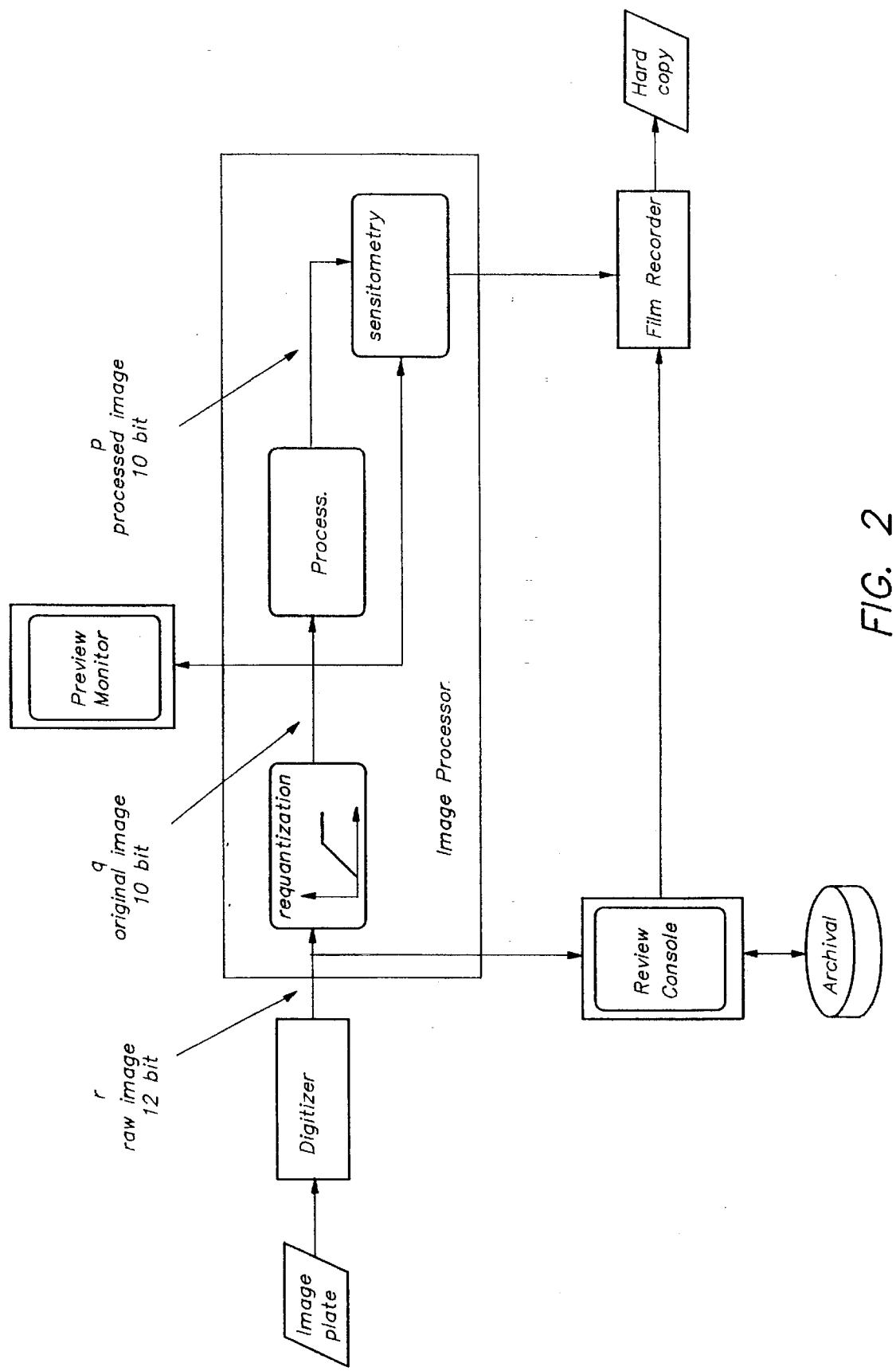
FIG. 2 illustrates the data path.

FIG. 1 generally shows an apparatus in which the method of the invention can be applied.

A radiographic image of an object or part thereof, e.g. a patient, is recorded onto a photostimulable phosphor plate by exposing (2) said plate to X-rays transmitted through the object. The stimulable phosphor plate is conveyed in a cassette (3), in the present embodiment the cassette is provided with a electrically erasable programmable read only memory (EEPROM). In an identification station 4 various kinds of data, for example patient identification data (name, date of birth) and data relating to the exposure and/or to the signal processing are recorded onto the EEPROM.

In a radiographic image read-out apparatus 1 the latent image stored in the photostimulable phophor sheet is read-out by scanning the phosphor sheet with stimulating rays emitted by a laser. The stimulating rays are deflected into the main scanning direction by means of a galvanometric deflection unit. The subscanning is performed by transporting the phosphor sheet in the subscanning direction. The stimulated emission is directed onto a photomultiplier for conversion into an electrical image representation.

Next, the signal is sampled and quantizised, this digital image is called the raw image. This digital image signal is sent to the image processor (FIG. 1, numeral 7) where it is stored in an internal buffer frame. Without any modifications it may also be sent from the image processor to a review console where it is temporarily stored on a hard disc. This back up ensures that the signal is never lost, even not when any of the components of the apparatus would fail and that the signal can be retrieved for any kind of later processing, for example processing with different parameter setting.

This feature will be used when the result of the on-line processing is unsatisfactory due to bad exposure conditions or inadequate selection of the processing parameters. The raw image can also be archived on optical disc (not shown).

At this stage the image is transmitted to the preview display 5 which gives a first impression of the acquired data and hence provides for early feedback to the operator in case the acquisition went wrong.

The raw image is next mapped to density values corresponding with an appropriate sensitometry possibly via a look up table and are applied to a digital to analogue converter, the output of the converter controls the modulator of a laser recorder 6 for making a hard-copy on photographic film.

Instead of being converted from a digital signal into an analogue signal e.g. via a programmable video digitizer, the image signals can also be transferred to the laser recorder in digital form through a digital interface.

An example of a laser recorder capable of accepting image signals in either analogue or digital form is the laser printer marketed by Agfa-Gevaert N.V. under the registered trade mark MATRIX COMPACT L.

This laser printer is suitable for recording the radiographic images generated by a digital radiographic system, or generated by other digital diagnostic techniques such as CT, MR and DSA.

Films suitable for being used in such laser printers are e.g. the photographic films marketed by Agfa-Gevaert N.V. under the registered trade marks SCOPIX LT, available in the following film formats: 8×10 in, 14×11 in or 14×17 in.

The image formats used in such laser printers are freely programmable. For square images, and 14×17 in film format the following formats are pre-programmable: 1/2/4/6/12/16/20.

Depending on the original (digital) image size (pixel matrix), selected film size and image format and amount of memory installed in the laser printer, the images will be rescaled to fit in the selected format. The maximum image size for a 1:1 reproduction or film depends on the film size and is as follows: for 8×10 in films: 2429×3044 pixels; for 14×11 in films: 4268×3353 pixels; for 14×17 in films: 4268×5182 pixels.

If a photostimulable radiographic plate is used of the quite commonly used size 14×17 in, a raw digital image being a 2048×2496 pixel matrix comprising 2048 pixels per line over 2496 lines is generated by the digital radiographic system.

Said pixel matrix is stored according to any of the techniques described above, and is visualised on the review (or preview) console or monitor as aforementioned.

The radiologist can then under visual control select the diagnostically relevant zone out of the global radiographic image viewed according to any of the methods described hereinafter. Such selection of the diagnostically relevant image zone before performing any digital processing on the pixel matrix to achieve image enhancement, has the advantage that the time consuming processing on the digital pixel matrix can be limited to that part of the pixel matrix corresponding to the selected diagnostically relevant image zone. The calculation time needed for such image enhancement processing functions may consequently drastically be reduced.

Now as is quite common in digital radiography, two images originating from one and the same recording on a stimulable phosphor plate may be recorded on one photographic film, one image e.g. corresponding to the raw original radiographic image, the other image resulting from the performance of one or more image enhancement processing functions. The total digital pixel matrix to be recorded on film then amounts to 2×(2048×2496) being (4096×4992).

If such pixel matrix is to be recorded on a 14×17 in film by a film recorder such as a laser printer, said digital image information is recorded by the laser printer in its internal (4268×5182) pixel matrix in such a way that when recording said radiogaphic images on film the two radiographic images are shown near to each other and are centered in the middle of the film. The pixel values in the laser printer's internal pixel memory out of the actual radiographic image data, are intentionally set to maximum density, such that when the two radiographic images are recorded on film, the outer margins of the film surrounding said radiographic images as well as a small strip between said two images are recorded at maximum density of the photographic film and consequently will appear as full black zones.

Figure 3:
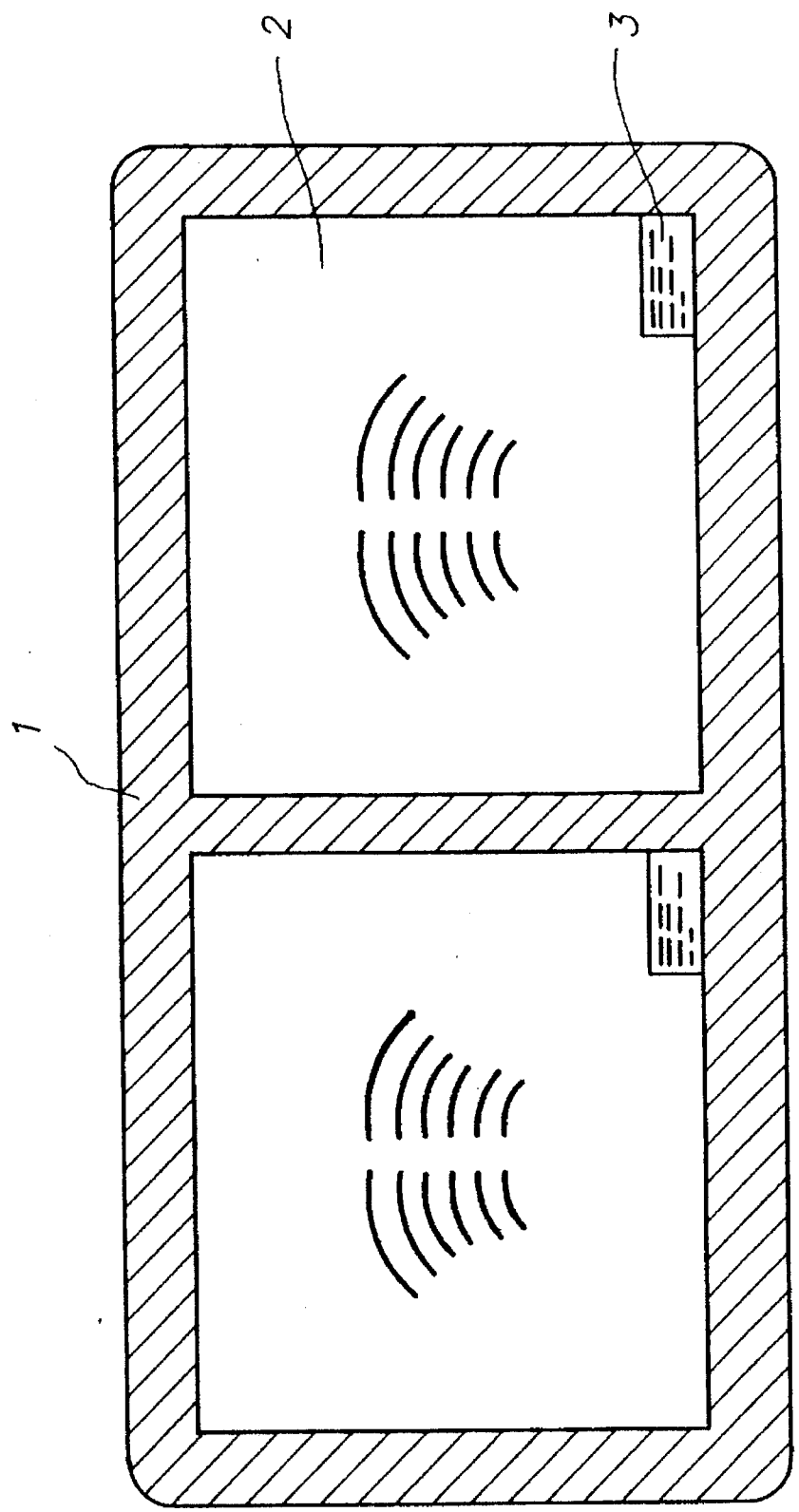
FIG. 3 illustrates a photographic film wherein radiographic images are recorded without applying the present invention.

FIG. 3 illustrates an output of a laser recorder of such two radiographic images recorded on one and the same photographic film. When such film is evaluated by a radiologist by visual inspection on an optical display unit such as a viewing box—or on a display unit such as a review console—the dazzling effect caused by the light transmitted trough those parts of the film around the diagnostically relevant part and having low density, is partially attenuated by the fact that the outer margins of the film as well as the center small stip between the two radiographic images aforementioned appear full black.

However, when a digital radiographic system is employed for diagnostical purposes, often the diagnostically relevant part is only a small fraction of the entire radiographic image; consequently the visual evaluation of that small relevant part is impaired by the dazzling caused by the surrounding light areas within the overall radiographic image.

As set forth above, when said diagnostically irrelevant or less 40 relevant image parts can be easily and practically determined by the radiologist and the density values of the image pixels comprised within said area are arbitrarily set to a density such that the light emitted by said remaining image parts is effectively masked off, an increased evaluation of detail in the diagnostically relevant image parts results.

An important step to be performed in carrying out the method of our invention is the determination of the diagnostically relevant image part(s) within the overall radiographic image. This function can be performed by the radiologist e.g. on the preview display monitor 5 aforementioned. Although a man-controlled way of operation is described hereinafter, it is clear that the functions set forth hereinafter may be readily automated. According to preferred embodiments of our invention, said diagnostically relevant image part(s) within the overall radiographic image may be determined according to any of the following methods.

In all three methods described hereinafter the radiographic image is first visualised on the screen of the preview monitor, a moveable light mark is generated on the screen of said monitor, and the motion of said light mark is synchronised with the motion of a marking means of a coordinate identification device such as a coordinate pen.

Now, according to a first embodiment, the diagnostically relevant image zone is defined as comprising all image points the coordinates whereof are comprised within a contour drawn by moving said light mark under visual control on the screen of the monitor.

According to a second embodiment an image point is marked as the upper left corner point and another image point is marked as the lower right corner point of the diagnostically relevant image zone. The coordinates of both said image points are determined and a rectangle on the basis of said coordinates is defined. Thereupon the diagnostically relevant image zone is defined as comprising all image points the coordinates whereof are comprised within said rectangle.

According to a third alternative embodiment one image point is marked as the center point and another image point is marked as the outer point of the diagnostically relevant image zone; after determining the coordinates of both said image points, the diagnostically relevant image zone is defined as comprising all image points the coordinates whereof are comprised within a circle, the center point whereof coincides with the image point marked as the center point of the diagnostically relevant image zone, and the radius whereof is defined by the vector distance between said center point and the other image point marked as the outer point of the diagnostically relevant image zone.

According to a fourth embodiment, various image points are marked as the corner points of the diagnostically relevant image zone, said zone being defined as comprising all image points the coordinates whereof are comprised within a polygone the cornerpoints whereof coincide with the image points marked as corner points of the diagnostically relevant image zone.

Whereas the first and fourth methods described have the advantage that the radiologist may define very accurately the diagnostically relevant image part, the second and third methods offer the advantage of ease of operation. It suffices to mark only two image points for defining the diagnostically relevant image part. Whereas the third method is suitable for being used when radiographic images of e.g. the skull have been taken, the second method can advantageously be used for radiographs e.g. of the chest.

The above methods of defining the diagnostically relevant parts in a radiographic image can be used either alone or in combination with each other, in case a radiographic image would comprise e.g. more than one diagnostically relevant zone.

Figure 4:
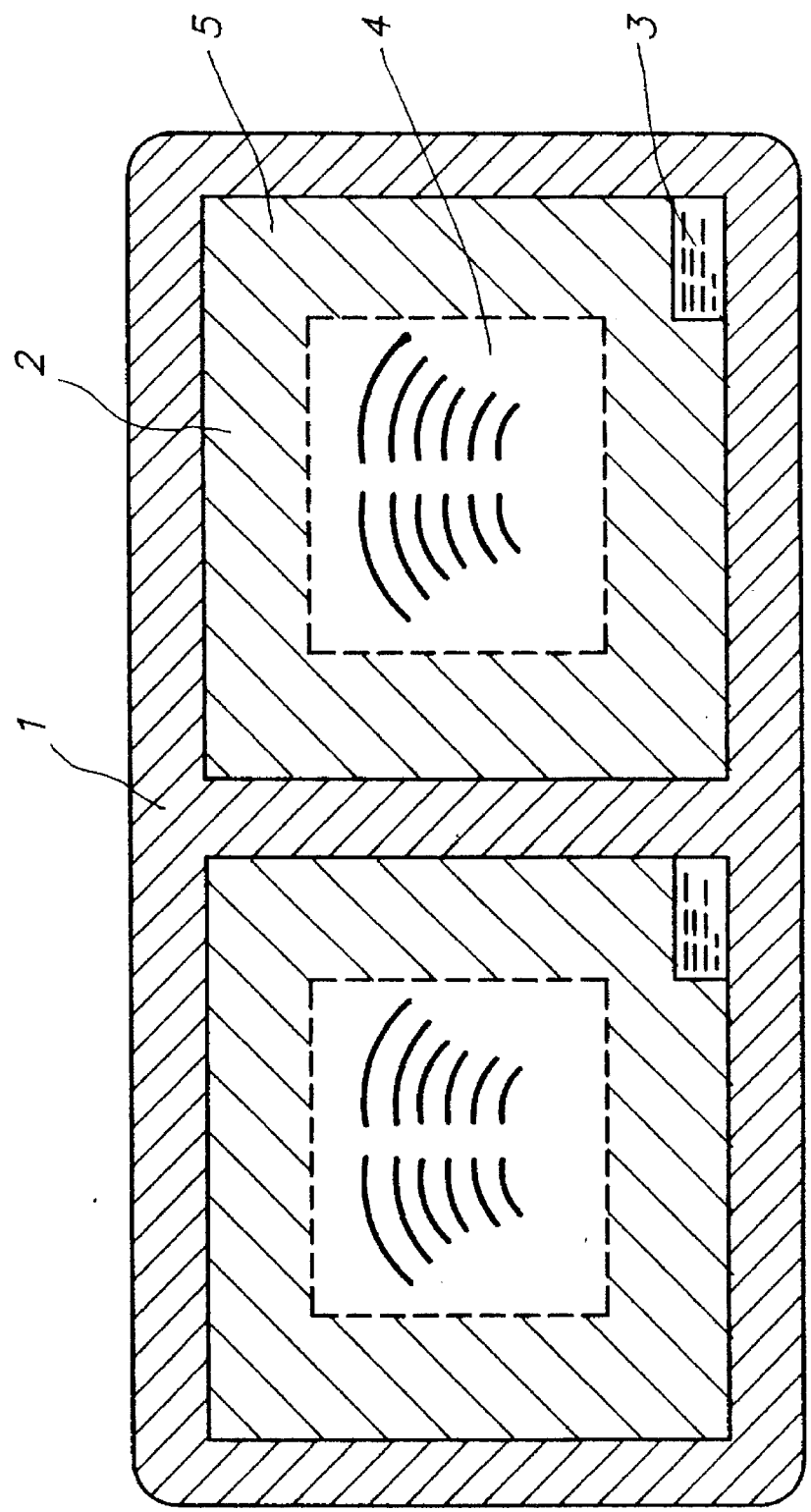
FIG. 4 illustrates a photographic film wherein radiographic images are recorded which were processed according to the method of the present invention.

FIG. 4 illustrates a photographic film wherein radiographic images are recorded whereupon the second method described above had been applied.

Within the overall chest radiographic image, a rectangle has been defined as encompassing the diagnostically relevant image, and the density of the image points situated out of said rectangle within the radiographic image, has been set to an arbitrary value, sufficiently high such that the light emitted by the diagnostically not relevant image zone situated between the diagnostically relevant zone and the black borders of the film and the black strip between the two radiographic images, is effectively masked off.

As a result, the diagnostic evaluation of the chest as recorded in the films shown in FIG. 4 was not impaired by the dazzling light caused by the light transmitted by the radiograph of FIG. 3 and enhanced detail could be observed in the radiographs of FIG. 4.

In FIG. 3:
 zone 1 represents the outer borders and small strip between two radiographic images,
 zone 2 represents the radiographic image, and
 zone 3 represents the corner in the radiographic image wherein the patient identification data are recorded.

In FIG. 4:
 zone 1, 2 and 3 represent the same as in FIG. 3,
 zone 4 represents the diagnostically relevant image zone within zone 2, and
 zone 5 represents the diagnostically not relevant image zone within zone 2.

The maximum density of photographic films used in laser recorders suitable for being linked to digital radiographic systems is usually situated between 3 and 4. The maximum density of the film marketed by Agfa-Gevaert N.V. under the registered trade mark SCOPIX LT 2B amounts to approximately 3.2. As the perceptability of the human eye to discern details generally decreases with increasing density of the image, the diagnostically relevant zone of the radiographic image should be recorded such that the density range thereof is situated between fog value of the photographic film and a density value situated between 1.5 and 3.0.

The outer borders and the small strips between the two radiographic images displayed on the photographic film are usually recorded at max. density of the photographic film.

In principle, the diagnostically not relevant image zone within the radiographic image could also be recorded at maximum density of the photographic film.

This however has the disadvantage that when the radiographic image would be recorded on film, all areas surrounding the diagnostically relevant part appear evenly black and the radiologist cannot see which zone of the radiographic image he has deliberately marked as being diagnostically not relevant. Therefore, according to a preferred embodiment of the present invention, said diagnostically not relevant zone within the overall radiographic image, should be recorded with a density between 0.5, preferably 1 and 2.5 preferably with a uniform density between said values. By doing so and as is illustrated in FIG. 4 three regions can be visually observed in the photographic film wherein the radiographic image is recorded:

the diagnostically relevant image parts within the radiographic image, recorded at densities preferably comprised between fog value of the photographic film and a maximum density situated between 1.5 and 3.0;

the diagnostically not relevant image zone within the radiographic image recorded in the photographic film with density comprised between 1 and 2.5; and the outer borders and small strip between two radiographic images recorded on the photographic film, all situated out of the radiographic image, recorded in the photographic film with uniform maximum density of said photographic film.

In case patient identification information is recorded on the photographic film concomitantly with the recording of the radiographic image, such as the patient name, registration number, radiologist's name, date, name of hospital and the like, such information is generally recorded in a corner of the radiographic image, generally comprised in the diagnostically not relevant image zone. Generally the patient identification information is recorded in the corner of the radiographic image particularly dedicated therefore in the form of black data (letters and figures) on a clear transparent film. This way of working however has the disadvantage mentioned supra i.e. that the dazzling effect described above still occurs.

In principle this drawback could be avoided by recording the patent identification information in the form of white data (letters and figures) on a black background. This method however has the disadvantage of bad readability under usual lighting conditions (e.g. in normal daylight).

Therefore according to a preferred embodiment of the present invention, whereas the density of the diagnostically not relevant image zone should be set a a density between 0.5, preferably 1 and 2.5, the density in the patient identification information zone should also be set to a sufficient high level so as to avoid the above described dazzling effect. In order to retain sufficient contrast in said corner required for easy reading of said information we have found that the—uniform—background density in said corner should be chosen between 0.5 and 1.5; consequently the electrical signals relating to the background of said patient identification corner and not relating to the actual patient identification data should be converted to a density comprised between 0.5 and 1.5. This is illustrated in FIG. 4.

Although the invention as described above relates to a method of processing suitable for being used in a radfogrpahic image system suitable for medical diagnosis, it may also be employed in a radiographic image system suitable for industrial (non-destructive testing) diagnostic applications.

We claim:

1. In a method of processing a radiographic image having diagnostically relevant and diagnostically non-relevant zones therein in a radiographic image recording system wherein image pixels constituting said radiographic image are converted into electrical signals corresponding substantially to the density values of the individual pixels and said electrical signals are employed for visualization of the radiographic image on a rendering medium, the improvement comprising the steps of establishing said diagnostically non-relevant zone of said image and adjusting the electrical signals of the image pixels comprised within said diagnostically non-relevant image zone of the radiographic image thus established to a generally uniform density value throughout said non-relevant image zone of at least about 0.5 such that when said radiographic image is visualized in said rendering medium from said electrical signals including the adjusted signals, the light transmitted by said diagnostically non-relevant image zone of the thus-visualized image is effectively masked off to reduce visual influence of the diagnostically non-relevant zone on the relevant zone during such visualization.

2. A method of processing according to claim 1 wherein said diagnostically relevant zone of said image is determined on a preview monitor screen and the diagnostically non-relevant image zone within the radiographic image is defined as encompassing all image pixels of the radiographic image that are not included within the thus-determined diagnostically relevant image zone.

3. A method of processing according to claim 2 wherein the diagnostically relevant image zone within the radiographic image is determined by a method comprising the following steps:
   a) visualizing the radiographic image on said preview monitor screen and identifying generally a diagnostically said relevant region of said radiographic image by inspection of said visualized image;
   b) generating on said preview monitor screen a moveable light spot the movement of which is synchronized with the motion of a marking means of a coordinate identification device; and
   c) moving said light spot on said screen under visual control around the border of said generally identified relevant region to thereby outline the contour of said relevant region of said image
   d) defining the diagnostically relevant image zone as comprehending all image pixels situated within the contour thus outlined.

4. A method of processing according to claim 2 wherein the diagnostically relevant image zone within the radiographic image is determined by a method comprising the following steps:
   a) visualizing the radiographic image on said preview monitor screen and identifying generally a rectangular shaped diagnostically relevant region by inspection of the thus-visualized radiographic image;
   b) generating on said preview monitor screen a moveable light spot the movement of which is synchronized with the motion of a marking means of a coordinate identification device;
   c) marking an image point as the upper left hand corner point of the thus-identified generally rectilinear region;
   d) marking another image point as the lower right corner of the thus-identified rectangular region;
   e) determining the coordinates of both said image points and determining a rectangle of the basis of the coordinates of said corner points; and
   f) defining the diagnostically relevant image zone as comprehending all image pixels situated within the thus-determined rectangle.

5. A method of processing according to claim 2 wherein the diagnostically relevant image zone within the radiographic image is determined by a method comprising the following steps:
   a) visualizing the radiographic image on said screen and identifying generally a circular shaped diagnostically relevant region by inspection of the thus-visualized radiographic image;
   b) generating on said preview monitor screen a moveable light spot the movement of which is synchronized with the motion of a marking means of a coordinate identification device;
   c) marking an image point as the center point of the thus-generally identified circular diagnostically relevant image region;
   d) marking another image point as the outer extent of generally identified circular diagnostically relevant region;
   e) determining the coordinates of both said image points; and
   f) defining the diagnostically relevant zone as comprehending all image pixels situated within a circle having as its center the image point marked as the center point of said circular diagnostically relevant image, and as its perimeter a circle passing through said another point of said circular diagnostically relevant region.

6. A method of processing according to claim 2 wherein the diagnostically relevant image zone within the radiographic image is determined by a method comprising the following steps:
   a) visualizing the radiographic image on said preview monitor screen and identifying generally a polygon shaped diagnostically relevant regionby inspection of the thus-visualized radiographic image;
   b) generating on said preview monitor screen a moveable light spot the movement of which is synchronized with the motion of a marking means of a coordinate identification device;
   c) marking a plurality of image points as plural corner points of said generally identified polygon shaped diagnostically relevant image region;
   d) determining the coordinates of said image points.

e) determining a polygon of predetermined configuration having corner points coinciding with the plurality of marked image points; and f) defining the diagnostically relevant image zone as comprehending all image pixels situated within the thus-determined polygon.

7. A method of processing according to claim 1, wherein the radiographic image visualized from said electrical signals including said adjusted signals is recorded by a film recorder as a hard copy on a photographic recording material.

8. A method of processing according to claim 7 wherein the film recorder is a laser recorder to which said electrical signals are delivered.

9. A method of processing according to claim 1 wherein the electrical signals of said image pixels comprised within the diagnostically non-relevant image zone within the radiographic image are adjusted to a generally uniform density value comprised between 0.5 and 2.5.

10. A method of processing according to claim 9 wherein the electrical signals of the image pixels comprised within the diagnostically non-relevant image zone within the radiographic image are adjusted to a generally uniform density value of at least 1.

11. A method of processing according to claim 1 wherein the electrical signals of the image pixels comprised within the diagnostically non-relevant image zone within the radiographic image are adjusted to a generally uniform density value comprised between 1.0 and 2.5 with the exception of patient data area reserved for recording patient identification data, said patient data image area being formed by a data image against a background, and the electrical signals for the background of the patient data area are adjusted to a generally uniform density between 0.5 and 1.5 while the electrical signals for the data image are adjusted to a generally uniform density contrasting with said background density.

12. A method of processing according to claim 1 wherein the electrical signals of border regions situated beyond the radiographic image are adjusted to maximum density value characteristic of the selected rendering medium.

13. A method of processing according to claim 7 wherein the electrical signals of the image pixels of the diagnostically relevant image zone are mapped to varying density values comprised between fog value characteristic of said photographic recording material and a density between 1.5 and 3.0.

14. A method of processing according to claim 1 wherein the radiographic image is created by exposing a stimulable phosphor plate to penetrating radiation attenuated by the object to be imaged and the exposed phosphor plate is scanned with a stimulating ray to read out the thus-created radiographic image and convert the same into electrical signals.

* * * * *